US00PP33820P3

(12) United States Plant Patent
Post

(10) Patent No.: US PP33,820 P3
(45) Date of Patent: Jan. 4, 2022

(54) ***CHRYSANTHEMUM* PLANT NAMED 'DLFUVIT7'**

(50) Latin Name: ***Chrysanthemum* X *morifolium***
Varietal Denomination: DLFUVIT7

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/170,628

(22) Filed: Feb. 8, 2021

(65) Prior Publication Data

US 2021/0251122 P1 Aug. 12, 2021

Related U.S. Application Data

(60) Provisional application No. 62/995,750, filed on Feb. 12, 2020.

(51) Int. Cl.
*A01H 5/02* (2018.01)
*A01H 6/14* (2018.01)

(52) U.S. Cl.
USPC ..... Plt./298
CPC ..... *A01H 6/1424* (2018.05)

(58) Field of Classification Search
USPC ..... Plt./298, 286, 297
See application file for complete search history.

*Primary Examiner* — Susan McCormick Ewoldt
(74) *Attorney, Agent, or Firm* — C. Anne Whealy

(57) ABSTRACT

A new and distinct cultivar of *Chrysanthemum* plant named 'DLFUVIT7', characterized by its upright plant habit; uniform growth habit; dark green-colored leaves; uniform and freely flowering habit; strong upright flowering stems; daisy-type inflorescences with purplish red purple-colored ray florets and yellow green-colored disc florets; resistance to Fusarium and White Rust; and good postproduction longevity.

2 Drawing Sheets

Figure 1:
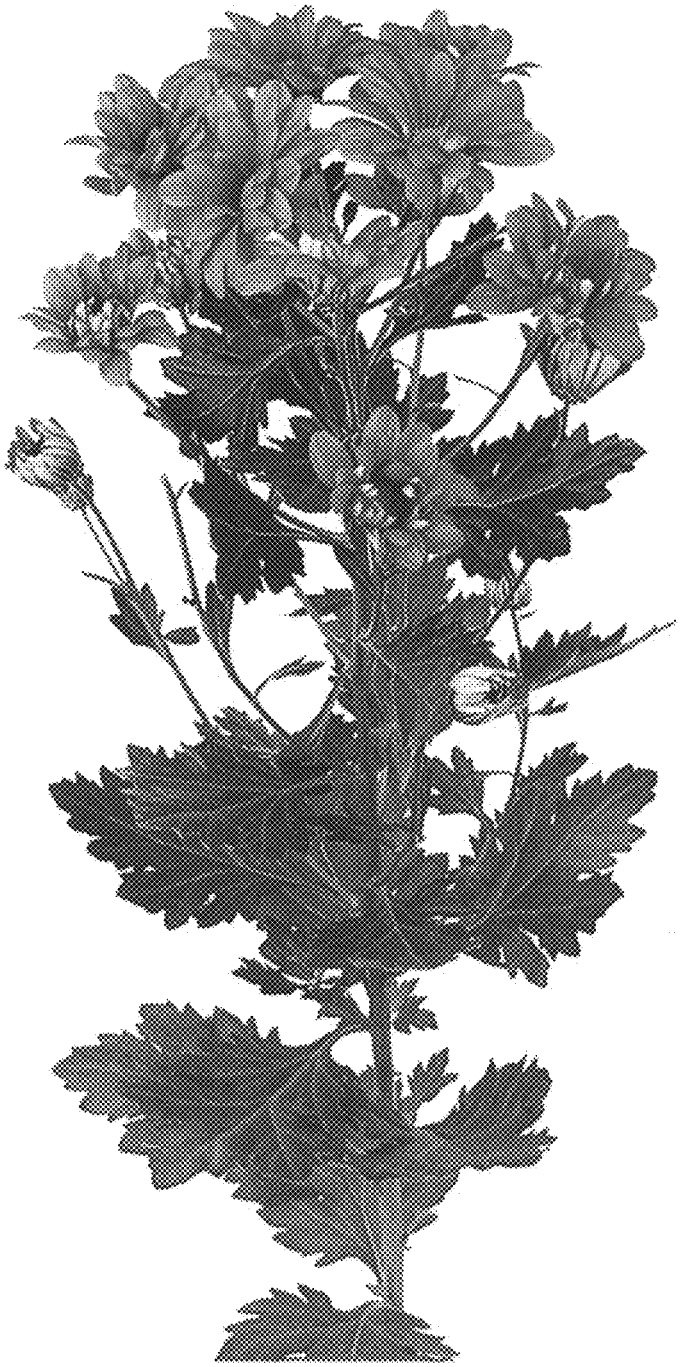

Botanical designation: *Chrysanthemum* X *morifolium*.
Cultivar denomination: 'DLFUVIT7'.

STATEMENT REGARDING PRIOR DISCLOSURES BY INVENTOR/APPLICANT & ASSIGNEE

A Columbian Plant Breeder's Rights application for the instant plant was filed by the Assignee, Deliflor Royalties B.V. of Maasdijk, The Netherlands on May 26, 2020, application number A202657. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFUVIT7'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant originated from a cross-pollination in September, 2013 of a proprietary selection of *Chrysanthemum* x *morifolium* identified as code number db 81052, not patented, as the female, or seed, parent with a proprietary selection of *Chrysanthemum* x *morifolium* identified as code number db 37566, not patented, as the male, or pollen, parent. The new *Chrysanthemum* plant was discovered and selected as a single flowering plant from within the progeny of the stated cross-pollination in a controlled greenhouse environment in Maasdijk, The Netherlands in April, 2014.

Asexual reproduction of the new *Chrysanthemum* plant by vegetative terminal cuttings since April, 2014 in a controlled greenhouse environment in Maasdijk, The Netherlands has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFUVIT7'. These characteristics in combination distinguish 'DLFUVIT7' as a new and distinct *Chrysanthemum* plant:

1. Upright plant habit; uniform growth habit.
2. Dark green-colored leaves.
3. Uniform and freely flowering habit.
4. Strong upright flowering stems.
5. Daisy-type inflorescences with purplish red purple-colored ray florets and yellow green-colored disc florets.
6. Resistant to Fusarium and White Rust.
7. Good postproduction longevity.

Plants of the new *Chrysanthemum* differ primarily from plants of the female parent selection in ray floret color as ray florets of plants of the new *Chrysanthemum* are purplish red in color whereas ray florets of plants of the female parent selection are deep red in color. In addition, ray florets of plants of the new *Chrysanthemum* have obtuse to shallowly retuse apices whereas ray florets of plants of the female parent selection have pointed apices.

Plants of the new *Chrysanthemum* differ primarily from plants of the male parent selection in ray floret color as ray florets of plants of the new *Chrysanthemum* are purplish red in color whereas ray florets of plants of the male parent selection are purplish pink in color. In addition, margins of ray florets of plants of the new *Chrysanthemum* are more involute than margins of ray florets of plants of the male parent selection.

Plants of the new *Chrysanthemum* can be compared to plants of *Chrysanthemum* X *morifolium* 'Chicle', not patented. In side-by-side comparisons, plants of the new *Chrysanthemum* differ primarily from plants of 'Chicle' in ray floret color as plants of the new *Chrysanthemum* have purplish red-colored ray florets whereas plants of plants of 'Chicle' have reddish purple-colored ray florets. In addition, ray florets of plants of the new *Chrysanthemum* have obtuse to shallowly retuse apices whereas ray florets of plants of 'Chicle' have emarginate apices.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) comprises a side perspective view of a typical flowering stem of 'DLFUVIT7' grown as a spray-type cut flower.

Figure 2:
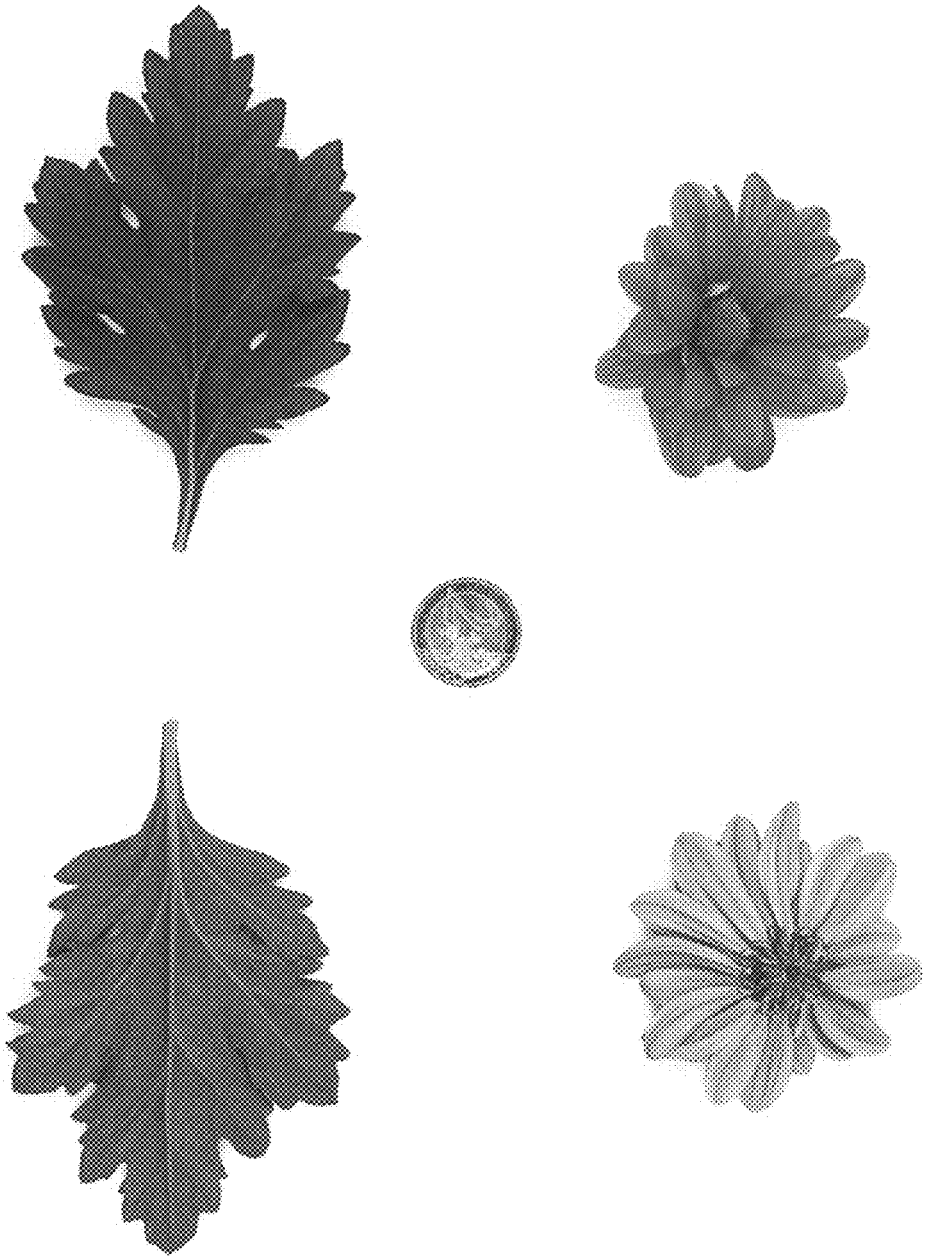

The photograph on the second sheet (FIG. 2) is a close-up view of upper (top of the photographic sheet) and lower (bottom of the photographic sheet) surfaces of typical leaves (left) and inflorescences (right).

DETAILED BOTANICAL DESCRIPTION

The aforementioned photographs and following observations and measurements describe plants grown during the late spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were eleven weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFUVIT7'.

Parentage:

*Female, or seed, parent.*—Proprietary selection of *Chrysanthemum* x *morifolium* identified as code number db 81052, not patented.

*Male, or pollen, parent.*—Proprietary selection of *Chrysanthemum* x *morifolium* identified as code number db 37566, not patented.

Propagation:

*Type.*—Terminal vegetative cuttings.

*Time to initiate roots, summer.*—About four days at temperatures about 20° C.

*Time to initiate roots, winter.*—About six days at temperatures about 20° C.

*Time to produce a rooted young plant, summer.*—About 13 days at temperatures about 20° C.

*Time to produce a rooted young plant, winter.*—About 15 days at temperatures about 20° C.

*Root description.*—Fine, fibrous; typically creamy white in color, actual color of the roots is dependent on substrate composition, water quality, fertilizers, substrate temperature and physiological age of roots.

*Rooting habit.*—Freely branching, medium density.

Plant description:

*Plant and growth habit.*—Herbaceous decorative-type cut flower that is typically grown as a single stem spray-type; upright plant habit; vigorous growth habit and rapid growth rate.

*Plant height, soil level to top of foliar plane.*—About 86.7 cm.

*Plant height, soil level to top of inflorescence plane.*—About 94.6 cm.

*Plant (spray) diameter.*—About 18.8 cm.

*Flowering stem length.*—About 85.2 cm.

*Flowering stem diameter.*—About 7 mm.

*Flowering stem internode length.*—About 2.5 cm.

*Flowering stem strength.*—Strong.

*Flowering stem aspect.*—Erect.

*Flowering stem texture and luster.*—Densely pubescent; slightly glossy.

*Flowering stem color, developing.*—Close to 144A.

*Flowering stem color, developed.*—Close to 146B; at the nodes, tinged with close to 152B.

*Leaf description.*—Arrangement: Alternate; simple. Length: About 12.3 cm. Width: About 8.4 cm. Shape, in outline: Broadly ovate to elliptic. Apex: Abruptly acute, minute. Base: Attenuate. Margin: Palmately lobed, coarsely serrate to dentate; sinuses convergent and medium to deep in depth. Texture and luster, upper surface: Moderately pubescent, not rugose; slightly velvety; slightly glossy. Texture and luster, lower surface: Densely pubescent, prominent venation; slightly velvety; very slightly glossy. Venation pattern: Pinnate, reticulate. Color: Developing leaves, upper surface: Close to 143A. Developing leaves, lower surface: Close to 146B. Fully developed leaves, upper surface: Slightly darker than NN137A; venation, close to 146B. Fully developed leaves, lower surface: Close to 147B; venation, close to 146B. Petioles: Length: About 1.7 cm. Diameter: About 3 mm by 4 mm. Strength: Moderately strong. Texture and luster, upper and lower surfaces: Moderately to densely pubescent; slightly glossy. Color, upper surface: Close to 147C; edges, close to NN137C. Color, lower surface: Close to 146B; edges, close to 147B. Stipules: Quantity and appearance: Two leafy stipules, opposite, at the petiole attachment to the stem. Length: About 7 mm. Width: About 2.5 mm. Shape, in outline: Lanceolate. Texture and luster, upper surface: Moderately pubescent; slightly glossy. Texture and luster, lower surface: Densely pubescent; very slightly glossy. Color: Upper surface: Slightly darker than NN137A; venation, close to 146B. Lower surface: Close to 147B; venation, close to 146B.

Inflorescence description:

*Appearance.*—Spray-type inflorescence form with obovate-shaped ray florets and tubular disc florets; inflorescences borne perpendicular to peduncles and face upright; ray and disc florets develop acropetally on a capitulum.

*Fragrance.*—Faintly fragrant; typical of *Chrysanthemums.*

*Flowering response.*—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 50 days later when grown as a spray-type.

*Postproduction longevity.*—Good postproduction longevity; after a seven-day storage period, cut flowers will maintain good color and substance for about 14 to 16 days in an interior environment; inflorescences persistent.

*Quantity of inflorescences.*—Typically grown as a spray-type, about 18 inflorescences develop per flowering stem.

*Inflorescence size.*—Diameter, grown as a spray-type: About 6.4 cm. Depth (height), grown as a spray-type: About 2.4 cm. Disc diameter: About 1.5 cm.

*Receptacles.*—Height: About 3 mm. Diameter: About 6 mm. Shape: Flattened globular. Color: Close to 145C.

*Inflorescence buds.*—Height: About 7 mm. Diameter: About 1.5 cm. Shape: Reniform. Texture and luster: Distally, smooth and glabrous; proximally, sparsely to moderately pubescent; slightly glossy. Color: Close to 137A to 137B and towards the base, close to 138A; immature ray florets, close to N77B.

*Ray florets.*—Quantity and arrangement: About 34 arranged in about two whorls. Length: About 3.9 cm, varying between 3.5 cm and 4.3 cm. Width: About 1.1 cm, varying between 0.8 cm and 1.2 cm. Shape: Obovate; mostly flat, slightly carinate. Apex: Obtuse to shallowly retuse. Base: Attenuate. Margin: Entire; not undulate. Aspect: About 10° to 60° from vertical. Texture and luster, upper surface: Smooth, glabrous; velvety; very slightly glossy. Texture and luster, lower surface: Smooth, glabrous; very slightly velvety; slightly glossy. Color: When opening, upper surface: Slightly darker than 71A. When opening, lower surface: Close to between 70A and 70B. Fully opened, upper surface: Close to 71A; towards the base, darker than 71A; venation, similar to lamina color; with development, color becoming closer to 71B. Fully opened, lower surface: Close to N75A to N75B; venation, similar to lamina color; color becoming closer to N75B to N75C with development.

*Disc florets.*—Quantity and arrangement: About 220 massed at the center of the receptacle. Length: About 6 mm. Diameter: About 1 mm. Shape: Lower 85% fused into a tube; upper 15% free. Apex: Narrowly acute. Margin, free-part: Entire. Texture and luster, inner and outer surfaces: Smooth, glabrous; glossy. Color, when opening, inner and outer surfaces: Close to 145C; towards the apex, close to 154D; at the apex, close to N144B. Color, fully opened, inner and outer surfaces: Close to 145C; towards the apex, close to 154D; apex tinged with close to N144B.

*Involucral bracts.*—Quantity and arrangement: About 22 arranged in about two whorls. Length: About 9 mm. Width: About 3 mm. Shape: Ovate to narrowly ovate. Apex: Obtuse. Base: Cuneate. Margin: Entire. Texture and luster, upper surface: Smooth, glabrous; glossy. Texture and luster, lower surface: Sparsely to moderately pubescent; matte. Color, upper surface: Slightly darker than 143A; lateral margins, translucent and close to 157C and apical margins, close to N199A. Color, lower surface: Close to 137A to 137B; lateral margins, translucent and close to 157D and apical margins, close to N199A.

*Peduncles.*—Length, terminal peduncle: About 6.2 cm. Diameter, terminal peduncle: About 3 mm. Length, third peduncle: About 7.1 cm. Diameter, third peduncle: About 3 mm. Strength: Strong. Aspect, terminal peduncle: Upright. Aspect, third peduncle: About 35° from the flowering stem axis. Texture and luster: Moderately pubescent; slightly glossy. Color: More intense than 143A.

*Reproductive organs.*—Androecium: Present on disc florets only. Quantity: About five per floret. Filament length: About 3 mm. Filament color: Close to 145B. Anther size: About 0.5 mm by 2 mm. Anther shape: Narrowly oblong. Anther color: Close to 151B. Pollen amount: Scarce. Pollen color: Close to 14A. Gynoecium: Present on both ray and disc florets. Quantity: One per floret. Pistil length: About 4.5 mm. Style length: About 4 mm. Style color: Close to N144D. Stigma diameter: About 1 mm. Stigma shape: Cleft, decurrent. Stigma color: Close to 153D. Ovary color: Close to 157C.

*Seeds and fruits.*—To date, seed and fruit production have not been observed on plants of the new *Chrysanthemum.*

Pathogen & pest resistance: Plants of the new *Chrysanthemum* have been observed to be resistant to Fusarium Wilt (*Fusarium oxysporum* spp. *chrysanthemi* (strain FoNL1)) and White Rust (*Puccinia horiana* P. Henn. (strain PhNL1)). To date, plants of the new *Chrysanthemum* have not been observed to be resistant to pests and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFUVIT7' as illustrated and described.

* * * * *